United States Patent [19]

Cornelius et al.

[11] Patent Number: 5,423,754
[45] Date of Patent: Jun. 13, 1995

[54] INTRAVASCULAR CATHETER

[75] Inventors: Richard G. Cornelius, Golden Valley; Matthew M. Burns, Orono, both of Minn.

[73] Assignee: SciMed Life Systems, Inc., Maple Grove, Minn.

[21] Appl. No.: 900,831

[22] Filed: Jun. 18, 1992

Related U.S. Application Data

[63] Continuation-in-part of Ser. No. 859,143, Mar. 27, 1992, abandoned, which is a continuation of Ser. No. 586,380, Sep. 20, 1990, Pat. No. 5,100,381.

[51] Int. Cl.6 ............... A61M 25/00; A61M 29/00
[52] U.S. Cl. .................. 604/103; 606/194; 604/96
[58] Field of Search ............... 604/96, 103; 606/194

[56] References Cited

U.S. PATENT DOCUMENTS

| | | |
|---|---|---|
| 3,448,739 | 8/1966 | Stark et al. |
| 4,024,873 | 5/1977 | Antoshkiw et al. |
| 4,177,815 | 12/1979 | Patel . |
| 4,323,071 | 4/1982 | Simpson et al. |
| 4,413,989 | 11/1983 | Schjeldahl et al. |
| 4,419,095 | 12/1983 | Nebergall et al. |
| 4,483,340 | 11/1984 | Fogarty et al. |
| 4,496,345 | 1/1985 | Hasson . |
| 4,545,390 | 10/1985 | Leary . |
| 4,582,181 | 4/1986 | Samson . |
| 4,597,755 | 7/1986 | Samson et al. |
| 4,646,742 | 3/1987 | Packard et al. |
| 4,741,328 | 5/1988 | Gabbay . |
| 4,781,681 | 11/1988 | Sharrow et al. |
| 4,782,834 | 11/1988 | Maguire et al. ............ 606/194 |
| 4,819,751 | 4/1989 | Shimada et al. |
| 4,820,349 | 4/1989 | Saab ............ 604/96 |
| 4,906,241 | 3/1990 | Noddin et al. ............ 606/194 |
| 4,921,483 | 5/1990 | Wijay et al. |
| 4,944,745 | 7/1990 | Sogard et al. |
| 4,955,895 | 9/1990 | Sugiyama et al. |
| 4,960,410 | 10/1990 | Pinchuk ............ 606/194 |
| 4,976,690 | 12/1990 | Solar et al. |
| 4,976,720 | 12/1990 | Machold et al. |
| 4,990,139 | 2/1991 | Jang . |
| 5,002,559 | 3/1991 | Tower ............ 606/194 |
| 5,041,089 | 8/1991 | Mueller et al. |
| 5,045,061 | 9/1991 | Seifert et al. ............ 606/194 |
| 5,046,503 | 9/1991 | Schneiderman . |
| 5,047,045 | 10/1991 | Arney et al. ............ 606/194 |
| 5,069,662 | 12/1991 | Bodden . |
| 5,100,381 | 3/1992 | Burns . |
| 5,100,386 | 3/1992 | Inoue . |
| 5,114,423 | 5/1992 | Kasprzyk et al. ............ 604/96 |
| 5,171,222 | 12/1992 | Eutenue ............ 606/194 |

FOREIGN PATENT DOCUMENTS

0405831A2 of 0000 European Pat. Off. .

OTHER PUBLICATIONS

"Schematic and Description of USCI Sprint PTCA Catheter" prepared by Rick Cornelius, Nov. 12, 1992.

Primary Examiner—Stephen C. Pellegrino
Assistant Examiner—Nancy Mulcare
Attorney, Agent, or Firm—Nawrocki, Rooney & Sivertson

[57] ABSTRACT

An over-the-wire angioplasty balloon catheter having a balloon bonded at its proximal and distal ends to an outer tubular member where the outer tubular member continues a guide wire lumen in the distal portion of the catheter. Alternatively, the balloon may have its proximal end bonded to an outer tubular member and its distal end bonded to an extension tubular member where the extension tubular member continues the guide wire lumen in the distal portion of the catheter or the balloon may be bonded at both its proximal and distal ends to the extension tubular member. Alternatively the inner tubular member may extend to the distal end of the catheter and both the proximal and distal ends of the balloon may be bonded to the inner tubular member.

2 Claims, 3 Drawing Sheets

INTRAVASCULAR CATHETER

The present invention is a continuation-in-part of U.S. patent Ser. No. 07/859,143, now abandoned, filed Mar. 27, 1992 entitled "Angioplasty Catheter" by Matthew M. Burns which is continuation of patent application Ser. No. 07/586,380, filed Sep. 20, 1992, now U.S. Pat. No. 5,100,381 issued Mar. 31, 1992 herein incorporated by reference.

BACKGROUND OF THE INVENTION

1. Field of the Invention

The present invention is directed to the field of angioplasty and, more particularly, to a coaxial dilation catheter having improved construction for greater maneuverability.

2. Description of the Prior Art

Angioplasty has gained wide acceptance in recent years as an efficient and effective method for treating certain types of vascular diseases. In particular, angioplasty is widely used for expanding a constricted area or lesion in a coronary artery. It is also used for treatment of lesions in other parts of the vascular system.

The most widely used form of angioplasty makes use of a balloon dilation catheter which is introduced into the patient's vascular system and is positioned across a stenosis. The balloon is inflated by supplying fluid under pressure through an inflation lumen connected to the balloon. The inflation of the balloon imparts a stretching force to the stenosis or artery wall to reestablish an acceptable blood flow through the artery.

There are various types of catheters available and one category of catheter is referred to as an over the wire (OTW) catheter. An OTW catheter is used in conjunction with a separate guide wire to cross a narrowed site in a person's vascular system. In this type of procedure, the guide wire is first advanced through the vasculature to or near the site of the lesion. After the guide wire is properly positioned, the catheter is advanced or guided over the guide wire so that the balloon portion is at the narrowed site.

OTW catheters may have a coaxial construction. The coaxial construction has an inner tube which defines an inner lumen and an outer tube coaxially disposed about the inner tube to define an outer lumen between the walls of the tubes. The inner lumen will typically have a guide wire running therethrough while the outer lumen conveys inflation fluid from the proximal end of the catheter to the inflatable balloon.

One advantage of the coaxial design is that the proximal portion of the outer tube can be formed of a relatively stiff material to provide increased pushability to the catheter. Another advantage is that the outer and inner tubes can be necked down in the distal region of the catheter and under the proximal waist of the balloon to reduce the distal shaft diameter and the profile of the balloon in its deflated state. Additionally, the inner and outer tubes can be necked over their distal lengths so as to increase the distal flexibility of the catheter. A further advantage is that the coaxial design is symmetrically flexible in all directions. In addition, the coaxial design allows a small degree of relative movement to take place between the inner tube and the outer tube when the catheter is bent further enhancing its flexibility.

Coaxial catheters may have various configurations. For example, the inner tube forming the guide wire lumen may continuously extend from the proximal end to the distal end of the catheter. The outer tube may be cut to a length so that it ends under the proximal waist of the balloon or it may be formed such that the balloon continues and completes the outer tube.

In another coaxial configuration, as described in Packard et al., U.S. Pat. No. 4,646,742, the outer tube extends from the proximal end to the distal end of the catheter and the balloon is bonded to the outer tube at both its proximal and distal waists. More specifically, the outer tube has a first predetermined diameter over a majority of its length and tapers down, in a transition zone, to a second predetermined diameter less than the first diameter which extends to the catheter's distal tip. A movable inner tube, coaxially disposed within the outer tube, has a distal end shaped to mate with the inside surface of the outer tube in the transition zone to form a seal when the inner tube is advanced in the distal direction. Ports are formed through the wall of the outer tube in the transition zone to convey inflation fluid to the inflatable balloon. When the inner tube is withdrawn from its sealing position, only a portion of the inflation fluid is available to fill the inflatable balloon and the remaining portion of the fluid perfuses out the distal end of the catheter.

It is desirable to provide a coaxial catheter having a reduced profile while maintaining the axial force required to cross a tight lesion. In addition, it is desirable to provide a coaxial catheter with varying flexibility characteristics in the proximal and distal regions of the catheter.

SUMMARY OF THE INVENTION

The coaxial catheter of the present invention includes an outer tubular member and an inner tubular member concentrically disposed in the outer tubular member to define an inflation lumen therebetween where the inner member defines a guide wire lumen in the proximal portion of the catheter and the outer member defines a guide wire lumen in the distal portion of the catheter. The outer tube has at least one aperture through its wall and an inflatable balloon is bonded at two spaced apart locations on either side of the aperture in the outer member.

Another preferred embodiment of the present invention, the coaxial catheter includes an outer tubular member and an inner tubular member concentrically disposed in the outer member to define an inflation lumen therebetween. The inner member terminates under the proximal waist of the balloon and has attached to its distal end an extension member. The extension member extends from the distal end of the inner tube to the distal end of the catheter. The outer tube terminates under the proximal waist of the balloon. The catheter is constructed by partially inserting at least one mandrel in the inflation lumen formed between the inner and outer tubes. The proximal waist of the balloon is positioned over the distal end of the outer tube and the distal waist of the balloon is coaxial with the extension tube. The mandrels extend from a point inside the inflation lumen of the catheter to a point distal of the distal end of the catheter. The proximal waist, outer tube, extension tube and inner tube are bonded together and create a seal around the mandrels. The mandrels are then removed creating apertures in the seal to allow communication between the inflation lumen and the interior of the balloon. Alternatively, polyimide or tef- Ion tubes may be used instead of mandrels and would not be removed after assembly.

In another preferred embodiment of the present invention, the coaxial catheter includes an outer tubular member and an inner tubular member concentrically disposed in the outer member to define an inflation lumen therebetween. The inner member terminates under the proximal waist of the balloon and has attached to its distal end an extension member. The extension member extends from the distal end of the inner tube to the distal end of the catheter. The distal end of the outer tube has approximately the same diameter as the proximal waist of the balloon. The catheter is assembled by partially inserting polyimide or teflon tubes in the inflation lumen formed between the inner and outer tubes. The proximal waist of the balloon is placed over the tubes and the proximal end of the extension tube. A small gap along the length of the shaft separates the distal end of the outer tube from the proximal waist of the balloon. The proximal waist of the balloon is bonded around the tubes to the extension tube. The distal end of the outer tube is bonded around the tubes to another portion of the extension tube.

In another preferred embodiment of the present invention, the coaxial catheter includes an outer tubular member and an inner tubular member concentrically disposed in the outer member to define an inflation lumen therebetween. The inner member, unlike the embodiment described previously, extends to the distal end of the catheter. The catheter is assembled in a similar manner as described with reference to the previous embodiment described above, however, the proximal waist of the balloon and the distal end of the outer tube are bonded to the inner tubular member instead of an extension member.

In another preferred embodiment of the present invention, the coaxial catheter includes an outer tubular member and an inner tubular member concentrically disposed in the outer member to define an inflation lumen therebetween. The inner member extends to the distal end of the catheter as described in the previous embodiment. The catheter is constructed in the same manner as described with reference to the previous embodiment with an additional step added after bonding the distal balloon waist. This additional step involves potting a high viscosity adhesive around the teflon or polyimide tubes between the distal end of the outer and the proximal balloon waist. This adhesive acts to somewhat stiffen this region of the catheter shaft.

In another preferred embodiment of the present invention, the coaxial catheter includes an outer tubular member and inner tubular member Concentrically disposed in the outer member to define an inflation lumen therebetween. The inner member extends to the distal end of the catheter as described in the previous embodiment. The catheter is constructed in a similar manner as described with reference to the previous two embodiments except the distal end of the outer tube is first bonded to the middle of the teflon or polyimide tubes by crimping and melting the outer tube around the tubes in a shape that still allows the inner tube to pass through the outer and beneath the crimped and melted region before passing into and through the balloon. The proximal waist of the balloon and the bonded distal end of the outer tube and tubes are then bonded to the inner tubular member.

In another preferred embodiment of the present invention, the coaxial catheter includes an outer tubular member and an inner tubular member concentrically disposed in the outer member to define an inflation lumen therebetween. The inner member extends to the distal end of the catheter as described above. The catheter is constructed by first joining together the tubes to form a single bridge assembly. The bridge assembly is then partially inserted in the inflation lumen formed between the inner and outer tubes. The proximal waist of the balloon and the distal end of the outer tube are then bonded to the bridge assembly and inner tubular member.

Further objects and advantages of this invention will become more apparent and readily appreciated from the following detailed description of the present invention with reference to the accompanying drawings.

DETAILED DESCRIPTION OF THE PREFERRED EMBODIMENTS

Figure 1:
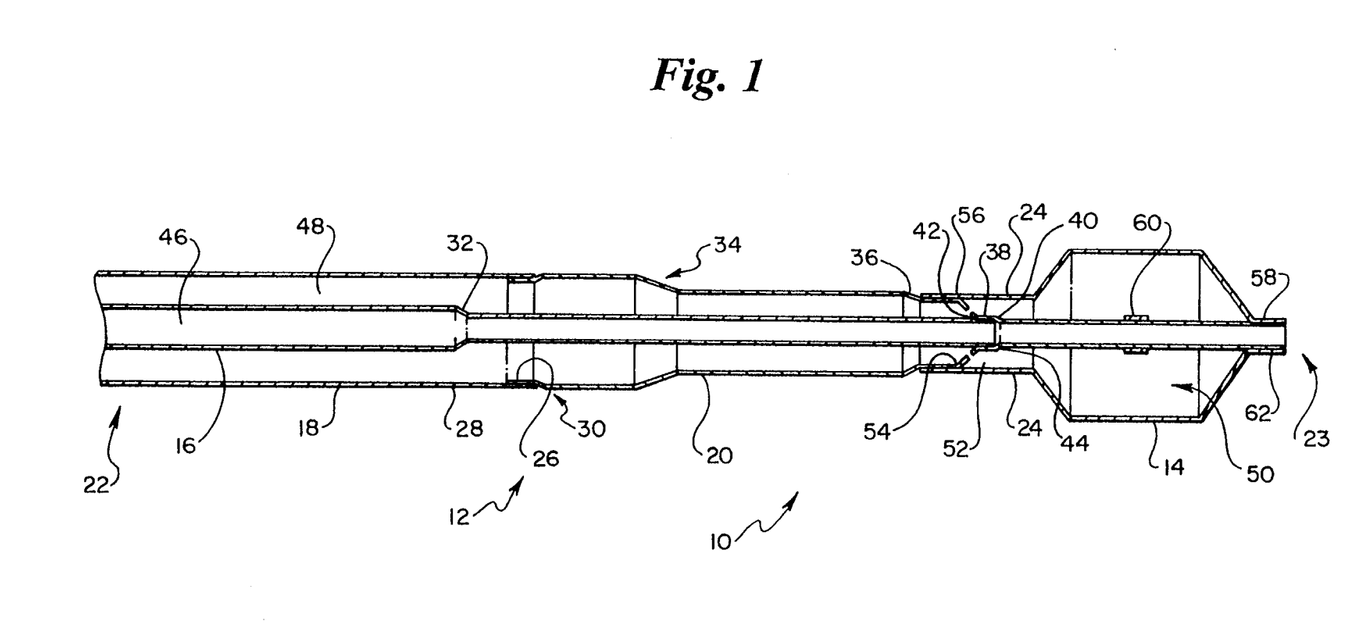
FIG. 1 is a cross-sectional view of a first preferred embodiment of the coaxial catheter according to the present invention.

FIG. 1 illustrates a cross sectional view of a coaxial dilation catheter 10 according to a first preferred embodiment of the present invention. The coaxial dilation catheter has a shaft 12 and an inflatable balloon 14. The shaft 12 has an inner tube 16, a proximal outer tube 18 and a distal outer tube 20. The inner tube 16 extends from the proximal end 22 of the shaft 12 and terminates proximal of the distal end 23 of the shaft 12. More specifically, the inner tube 16 preferably terminates under the proximal waist 24 of the balloon 14.

The inner tube 16 is preferably constructed of polyethylene (PE) and more preferably a high density PE. The proximal and distal outer tubes 18 and 20 respectively are coaxially disposed around the inner tube 16. The proximal outer tube 18 is preferably stiffer than the distal outer tube 20. Preferably the proximal outer tube 18 is fabricated from a high density PE, a polyamide encased stainless steel braid or a hypotube. The distal outer tube 20 is preferably fabricated from a polyethylene (PE) and more preferably a high density PE. The distal portion of the catheter 10 has greater flexibility than the proximal portion of the catheter 10 due to the material transition and the dimensional transition in the shaft 12.

The proximal end 26 of the distal outer tube 20 is bonded to the distal end 28 of the proximal outer tube 18. Preferably, the distal outer tube 20 is necked to a smaller diameter at point 30 so that a portion of the proximal outer tube 18 fits over a portion of the distal outer tube 20. The process of necking tubing to a reduced diameter is well known to those skilled in the art. Generally, a tapered die is used which is heated to approximately the glass transition temperature of the tubing or slightly above and the end of the tubing is inserted into the die and pulled through the die. Necking of the tubing is thus accomplished by a combination of temperature at or above the glass transition temperature of the extrusion and a minimal applied tensile force. The proximal outer tube 18 has an inner diameter of about 0.033" and an outer diameter of about 0.040". The distal outer tube 20 distal of connection point 30 has an inner diameter of about 0.032" and an outer diameter of about 0.040". The proximal outer tube 18 is approximately 43" in length whereas the distal outer tube 20 is 12" in length.

There are several ways to bond the proximal and distal outer shafts at bond 26. Preferably, a urethane adhesive such as Urethane 3549 available from the 3M Company of St. Paul, Minn. or Urethane 3507 available from the H. B. Fuller Company of St. Paul, Minn. is used to bond the outer tubes 18 and 20. A strain relief (not shown) may be fitted over the bond 26 between the proximal outer tube 18 and the distal outer tube 20. The strain relief is preferably a wrapped stainless steel ribbon covered by a thin heat-shrunk polymer sleeve. The strain relief provides additional strength at the bond between shafts 18 and 20, particularly when tension is applied to the bond.

While the catheter shown in FIG. 1 has an outer shaft formed of multiple sections in the form of proximal outer tube 18 and distal outer tube 20, the outer shaft may, alternatively, be formed by one single tubular member.

The inner tube 16 is necked down to a reduced diameter at point 32. This allows the catheter 10 to have a reduced profile in the distal portion of the catheter 10 as will be described in detail hereinafter. Point 32 is located approximately 41" from the proximal end 22 of the shaft 12.

The distal outer tube 20 is necked down to a reduced diameter at several locations. At point 34 the outer tube 20 is necked from a first diameter approximately equal to 0.040" to a second diameter having an outer diameter preferably of about 0.036". At point 36 the outer tube 20 is again necked to a third outer diameter, the third diameter being less than the inner diameter of the proximal waist 24 of the balloon 14 so that the outer tube 20 fits under the proximal waist 24 of the balloon 14. The outer tube 20 at point 36 preferably has an inner diameter of about 0.028" and an outer diameter of about 0.033". At point 38 the outer tube 20 is again necked to a fourth diameter. At this point, the outer tube 20 preferably has an outer diameter of about 0.029" and an inner diameter of about 0.024". The inner tube 16 at point 38 has an outer diameter of about 0.0226", thus the inner surface 40 of the outer tube 20 is in close proximity to the outer surface 42 of the inner tube 16. Finally at point 44 the outer tube 20 is necked to a fifth diameter preferably substantially equal to the diameter of the inner tube 16. Preferably, at point 44 the outer tube 20 has an inner diameter of about 0.01165" and an outer diameter of about 0.0225". Point 34 is located approximately 5 inches from the proximal end 26 of the outer tube 20. Point 36 is located approximately 7 inches from point 34, point 38 is located approximately 4 mm from point 36 and point 44 is located approximately 4 mm from point 38. The proximal waist 24 of the balloon 14 is approximately 10 mm in length.

The inner tube 16 defines a lumen 46 for disposing therein a guide wire (not shown). The catheter 10 according to the present invention is intended to be used with standard sized guide wires, therefore, the proximal portion of the inner tube has preferably an inner diameter of about 0.018" and an outer diameter of about 0.025" while the distal portion of the inner tube 16 has preferably an inner diameter of about 0.0165" and an outer diameter of about 0.0215". To reduce friction between the guide wire lumen wall and the guide wire, the inner surface of the guide wire lumen 54 may be coated with a hydrophobic coating (i.e. silicone) or a hydrophilic coating (i.e. P.V.P.).

Disposed between the inner tube 16 and the outer tube 20 is a lumen 48 used to convey inflation fluid to the interior 50 of the balloon 14. While not illustrated, the proximal end 22 of the catheter 10 is connected to a manifold having an inflation port (not shown) and a guide wire port (not shown) as is well known by those skilled in the art. The inflation port delivers the inflation fluid to the inflation lumen 48. The proximal portion of the shaft 12 and manifold are secured together by suitable adhesive bonding means such as Urethane 3549 available from the 3M Corporation described above. Inflation fluid is conveyed to the interior 50 of the balloon 14 through apertures 52 located in the wall 54 of the outer tube 20 between points 36 and 38. Preferably, three or four apertures 52 are provided each preferably having a diameter of about 0.004". In order to deflate the balloon 14, a vacuum source (not shown) is connected with the lumen 48 so that the inflation fluid in the interior 50 of the balloon 14 is removed along the same path in which the inflation fluid was initially delivered to the interior 50 of the balloon 14.

A suitable balloon material is a polyolefin which has been treated by radiation crosslinking. A suitable polyolefin is available from E. I. DuPont de Nemours & Co. located at Wilmington, Del. under the trade name SURLYN® Ionomer as Resin No. 8527. Other suitable materials include a polyethylene terephthalate or a ethylene vinyl acetate. The balloon 14 is preferably bonded to the outer tube 20 at points 56 and 58 by an adhesive such as Urethane 3507 available from the H. B. Fuller Company as described above.

At point 38, the inner tube 16 terminates and the outer surface 42 of the inner tube 16 is preferably bonded to the inner surface 40 of the outer tube 20 by either an adhesive such as Urethane 3507 as described above or a heat bond using RF or resistance heating.

The guide wire lumen 46 formed by the inner tube 16 is thus continued at point 38 by the outer tube 20 so that the guide wire lumen 46 continuously extends from the proximal end 22 of the catheter 10 to the distal end 23 of the catheter 10. The guide wire lumen 46 is thus defined by two tubes which preferably have different flexibility characteristics. The different characteristics may arise because different materials are used for the inner 16 and outer 20 tubes or the dimensions of the inner tube 16 may be different from that of the distal outer tube 20. Continuing the outer tube 20 to the distal tip 23 of the catheter 10 allows the outer tube 20 to transmit the axial force required to cross a tight lesion to the tip 23 of the catheter 10 instead of the inner tube 16. This reduces the required column strength of the inner tube 16 and allows thinner walled tubing to be used for the inner tube 16. Using a thinner walled inner tube 16 reduces the overall diameter of the catheter shaft 12. In one preferred embodiment the inner tube 16 is a polyethylene tubing with walls ranging from 0.0015" to 0.004". In another embodiment, the inner tube 16 is a very thin walled polyimide tubing with a teflon coating on the inner diameter of the inner tube 16. The inner tube 16 has a wall thickness preferably ranging from 0.001" to 0.0015".

A platinum marker band 60 is provided around the outer tube 20 in the interior region 50 of the balloon 14 so that the position of the catheter 10 can be seen by X-ray as is well known to those skilled in the art.

Preferably the proximal waist 24 of the balloon 14 is joined to the outer tube 20 and the distal waist 62 of the balloon 14 is joined to the distal end of the outer tube 20 by a heat seal. Generally, there are two methods of creating a heat seal and both are well known to those skilled in the art. The first method is to shrink the proximal waist 24 and the distal waist 62 of the balloon 14 around the outer tube 20. This method is preferred if the balloon material and the shaft material are not compatible. The second method is to weld the proximal 24 and distal waists 62 of the balloon 14 onto the outer tube 20. This method is preferred if the balloon 14 material and the outer tube 20 material are compatible and the materials will actually mix when heated. The heat source for either shrinking or welding the balloon 14 to the catheter shaft 12 preferably utilizes RF or resistive heating.

The shaft 12 is preferably provided with a lubricous coating to reduce frictional resistance between the vessel lumen and the outer surface of the catheter 10. If the proximal portion of the outer tube 18 is formed of metal, polytetrafluoroethylene is preferably applied to that portion of the shaft 12 to reduce friction. The balloon 14 may also have a lubricous hydrophobic, i.e. silicone or hydrophilic, i.e. PVP coating applied thereto. A suitable coating thickness is about t=0.0005" for Teflon and t=0.00005" for silicone or PVP.

In addition, preferably some of the plastic parts of the catheter 10 are plasma treated to increase their bonding characteristics. For example, the shaft 12 and manifold (not shown) may be plasma treated using helium or oxygen plasma treating techniques.

Figure 2:
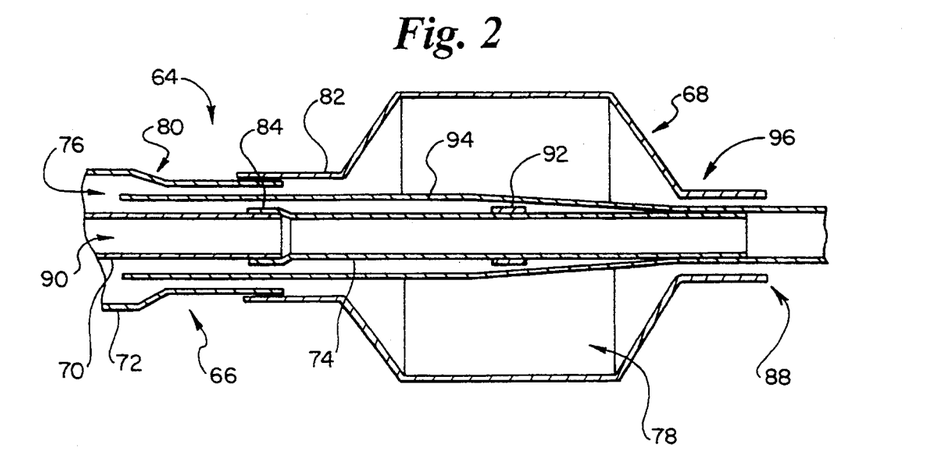
FIG. 2 is a cross-sectional view of a second preferred embodiment of a partially constructed coaxial catheter according to the present invention.

FIG. 2 illustrates a partially constructed catheter 64 according to a second preferred embodiment of the present invention. The catheter 64 comprises a shaft 66 and an inflatable balloon 68. The shaft 66 has an inner tube 70, an outer tube 72 and an extension tube 74. The inner tube 70 and extension tube 74 are of sufficient diameter to house a standard guide wire (not shown) therein as described with reference to the inner tube of FIG. 1. The outer tube 72 defines an annular lumen 76 about the inner tube 70 and a portion of the extension tube 74 wherein inflation fluid from an inflation port in a manifold (not shown) is conveyed to the interior 78 of the balloon 68. The outer tube 72 may be formed of multiple sections as illustrated in FIG. 1 or, alternatively, it may be formed by one single tubular member. The outer tube 72 is necked to a smaller diameter at point 80 to fit under the proximal waist 82 of the balloon 68. The outer tube 72 terminates under the proximal waist 82 of the balloon 68. The inner tube 70 also preferably terminates under the proximal waist region of the balloon 68. In a preferred embodiment, both tubes terminate at the same point under the proximal waist region of the balloon 68.

The proximal waist 82 of the balloon 68 is located approximately 54" from the proximal end (not shown) of the shaft 66. The proximal waist 82 of the balloon 68 is approximately 10 mm in length.

The proximal end 84 of the extension tube 74 fits over a portion of the inner tube 70 at a point located under the proximal waist region of the balloon 68. The extension tube 74 therefore preferably has an inner diameter greater than the outer diameter of the inner tube 70. The inner tube 70 preferably has an outer diameter of about 0.0215" and an inner diameter of 0.0165" and the extension tube 74 preferably has an outer diameter of about 0.0270" and an inner diameter of about 0.023". The extension tube 74 is necked to a smaller diameter distally from the distal end of the inner tube 70 and extends from the proximal waist region of the balloon 68 to the distal end 88 of the catheter 64. The necked extension tube 74 preferably has the same dimension as the inner tube 70 as described above. The guide wire lumen 90 defined by the inner tube 70 is thus continued by the extension tube 74 in the balloon region of the catheter 64. The extension tube 74 is approximately 2" in length.

A platinum marker band 92 is provided around extension tube 74 in the interior region 78 of the balloon 68 so that the position of the catheter 64 can be seen by X-ray as is well known to those skilled in the art.

The construction of catheter 64 according to this second preferred embodiment will now be described. The extension tube 74 is fitted over the distal portion of the inner tube 70. Mandrels 94 are partially inserted in the inflation lumen 76 formed between the inner and outer tubes. The balloon 68 is positioned so that its proximal waist 82 surrounds the necked portion of the outer tube 72 and its distal waist 96 is coaxial with the extension tube 74. The mandrels 94 thus extend from a point inside the inflation lumen 76 of the catheter 64 to a point distal of the distal end 88 of the catheter 64.

The catheter 64 is assembled by applying a heat weld to the proximal waist 82 of the balloon 68 as is well known to those skilled in the art. The heat causes the interior surface of the proximal waist 82 of the balloon 68 to create a seal to the outer surface of the necked portion of the outer tube 72 which seals around the mandrels 94 to the outer surface of the extension tube 74 which seals to the outer surface of the inner tube 70. After the heat seal is applied to the proximal waist 82 of the balloon 68, the mandrels 94 are pulled out of the inflation lumen 76. When the mandrels 94 are removed, aperatures are created in the region of the heat weld which allow for communication between the inflation lumen 76 and the interior 78 of the balloon 68.

The distal waist 96 of the balloon 68 is then bonded to the distal end 88 of the catheter 64 preferably by an adhesive such as a urethane adhesive, as described above, or an epoxy such as Tracon BA 2135D available from Tracon of Medford, Mass. Although two mandrels 94 have been illustrated, the number of mandrels used is determined by the number of apertures desired to provide access to the interior 78 of the balloon 68. In addition, while mandrels 94 are shown as located 180° from one another on opposite sides of the inner tube 70, they may be located on the same side of the inner tube.

As an alternative to mandrels 94, small teflon tubes, polyimide tubes or any other material that has a higher melting temperature than the shaft and balloon materials can be used. When tubes are used, however, they do not have to be removed but rather form a part of the catheter as will be appreciated from the description with reference to FIGS. 3-9. An adhesive bond using, for example, Urethane 3549 described above, is possible when tubes are used instead of the mandrels.

An advantage of this preferred embodiment is that the extension tube 74 does not have to be formed from the same material as the inner tube 70 or the outer tube 72. The extension tube 74 is preferably constructed of a material more flexible than the outer tube 72 so that the distal portion of the catheter 64 remains flexible and thus had greater maneuverability.

Figure 3:
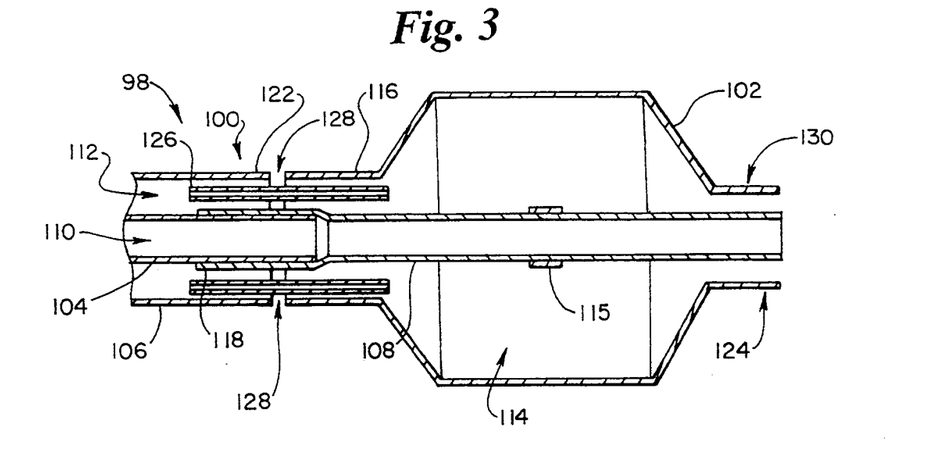
FIG. 3 is a cross-sectional view of a third preferred embodiment of a partially constructed coaxial catheter according to the present invention.

FIG. 3 illustrates a partially constructed catheter 98 according to a third preferred embodiment of the present invention. The catheter 98 comprises a shaft 100 and an inflatable balloon 102. The shaft 100 has an inner tube 104, an outer tube 106 and an extension tube 108. The inner tube 104 and extension tube 108 form a guide wire lumen 110 of sufficient diameter to house a standard guide wire (not shown) therein. The outer tube 106 defines an annular lumen 112 about the inner tube 104 and a portion of the extension tube 108 wherein inflation fluid from an inflation port in a manifold (not shown) is conveyed to the interior 114 of the balloon 102. The outer tube 106 may be formed of multiple sections as illustrated in FIG. 1, or alternatively, it may be formed by one single tubular member. The outer tube 106 has an inner diameter substantially equal to that of the proximal waist 116 of the balloon 102. The inner tube 104 preferably terminates under the proximal waist region 116 of the balloon 102.

The proximal end 118 of the extension tube 108 fits over a distal portion of the inner tube 104 located generally under the distal end 122 of the outer shaft 106 and proximal waist 116 of the balloon 102. The extension tube 108 thus preferably has an inner diameter greater than the outer diameter of the inner tube 104 at the proximal end 118 of the extension tube 108 so that the extension tube 108 fits over the distal end of the inner tube 104. The inner tube 104 preferably has an outer diameter of about 0.0215" and an inner diameter of about 0.0165". The extension tube 108 preferably has an outer diameter of about 0.0270" and an inner diameter of about 0.023" in the region surrounding the inner tube 104. The extension tube 108 is necked to a smaller diameter distally from the distal end of the inner tube 104. The necked extension tube 108 preferably has the same dimensions as the inner tube 104 described above. The extension tube 108 thus extends from the proximal waist region of the balloon 102 to the distal end 124 of the catheter 98. The guide wire lumen 110 defined by the inner tube 104 is thus continued by the extension tube 108 in the interior region 114 of the balloon 102. Alternatively, the inner tube 104 can extend through the interior of the balloon 102 to the distal end 124 of the catheter 98 thereby eliminating the use of extension tube 108 as will be described with reference to FIG. 4.

A platinum marker band 115 is provided around the extension tube 108 in the interior region 114 of the balloon 102 as described above.

The construction of catheter 98 according to this third preferred embodiment will now be described. The extension tube 108 is fitted over the distal end of the inner tube 104. Polyimide or teflon tubes 126 preferably having an outer diameter of about 0.005" and an inner diameter of 0.003" and a length of 0.5" are partially inserted in the inflation lumen 112 formed between the inner and outer tubes. The tubes 126 are preferably placed on opposite sides of the inner tube 104. The proximal waist 116 of the balloon 102, which has approximately the same inner diameter as the outer tube 106, is placed over the tubes 126 and the extension tube 108. A small gap 128 separates the proximal waist 116 of the balloon 102 from the distal end of outer tube 106. The gap 128 is approximately 5 mm in length. The position of the proximal waist 116 of the balloon 102 is approximately the same distance from the proximal end (not shown) of the shaft 100 as described above with reference to FIG. 2. The distal waist 130 of the balloon 102 is coaxial with the distal end of the extension tube 108. The tubes 126 thus bridge the distal end of the outer tube 106 to the proximal waist 116 of the balloon 102.

The catheter 98 is assembled by applying a heat weld, as is well known by those skilled in the art, to the distal end of the outer tube 106 to seal the outer tube 106 around the polyimide or teflon tubes 126 to the extension tube 108. The proximal waist 116 of the balloon 102 is then bonded to the extension tube 108 with a urethane adhesive such as Urethane 2139 available from the H. B. Fuller Company, thereby sealing the proximal waist 116 of the balloon 102 around the polyimide or teflon tubes 126 to the extension tube 108. The polyimide or teflon tubes 126 are used to allow the inflation lumen 112 to communicate past the distal end of the outer tube 106 with the interior of the balloon 102. The tubes 126, unlike the mandrels described above, are not removed after the heat welding and bonding. Alternatively, the seal between the outer and inner tubes could be achieved with an adhesive bond using an adhesive such as H. B. Fuller 2139 as described above.

The distal waist of the balloon 102 is then bonded to the distal end of the extension tube 108 preferably by a urethane adhesive such as H. B. Fuller 3507 or an epoxy such as Tracon BA 2135D described above.

Although two polyimide or teflon tubes 126 have been illustrated, the number of tubes used is dictated by the amount of communication desired between the inflation lumen 112 and the interior of the balloon 102. As will be illustrated with reference to FIGS. 6-9, the polyimide or teflon tubes do not have to be placed on opposite sides of the inner tube.

This embodiment has similar advantages as the catheter shown in FIG. 2, namely, the extension tube 108 does not have to be formed from the same material as the inner tube 104 or the outer tube 106. The extension tube 108 is preferably constructed of a material more flexible than the outer tube 106 so that the distal portion of the catheter 98 remains flexible and more maneuverable.

Figure 4:
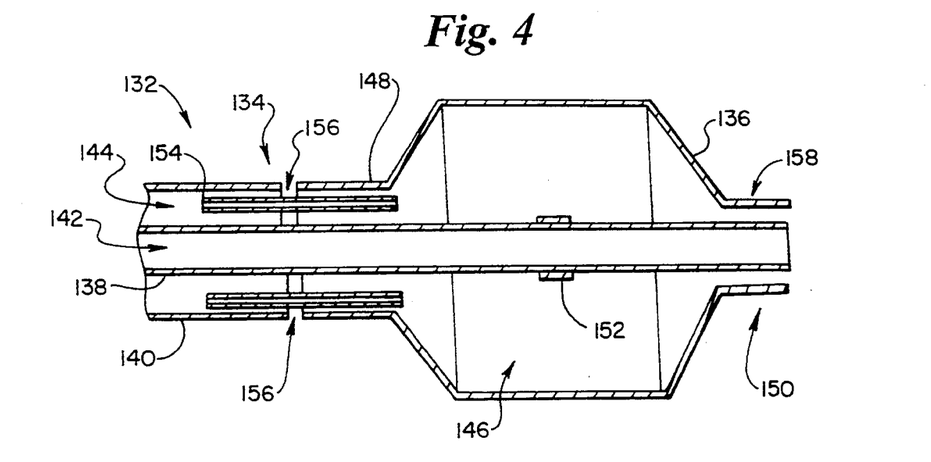
FIG. 4 is a cross-sectional view of a fourth preferred embodiment of a partially constructed coaxial catheter according to the present invention.

FIG. 4 illustrates a partially constructed catheter 132 according to a fourth preferred embodiment of the present invention. The catheter 132 comprises a shaft 134 and an inflatable balloon 136. The shaft 134 has an inner tube 138 and an outer tube 140. The inner tube 138 forms a guide wire lumen 142 of sufficient diameter to house a standard guide wire (not shown) therein. The outer tube 140 defines an annular lumen 144 about the inner tube 138 wherein inflation fluid from an inflation port in a manifold (not shown) is conveyed to the interior 146 of the balloon 136. The outer tube 140 may be formed of multiple sections as illustrated in FIG. 1, or alternatively, it may be formed by one single tubular member. The outer tube 140 has an inner diameter substantially equal to that of the proximal waist 148 of the balloon 136.

Unlike the catheter shown in FIG. 3, the inner tube 138 of the catheter according to FIG. 4 extends through the interior 146 of the balloon 136 to the distal end 150 of the catheter 132. The inner tube 138 preferably has an outer diameter of about 0.0225" and an inner diameter of about 0.0165".

A platinum marker band 152 is provided around the inner tube 138 in the interior region 146 of the balloon 136 as described above.

Figure 5:
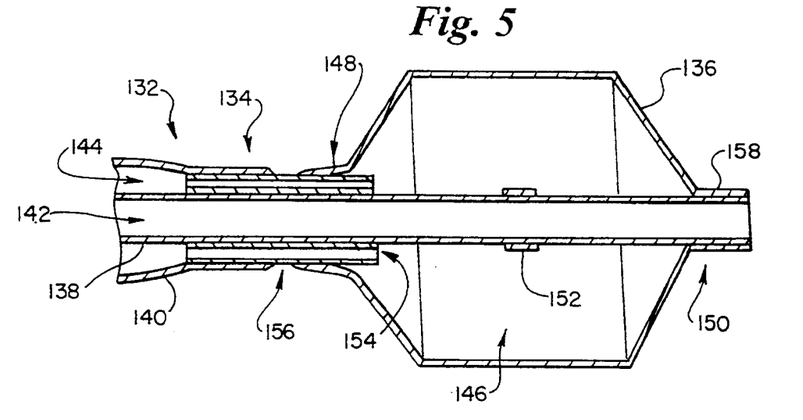
FIG. 5 is a cross-sectional view of the catheter of FIG. 4 constructed according to the present invention.

The construction of the catheter 132 according to this fourth preferred embodiment will now be described with reference to FIG. 5. Polyimide or teflon tubes 154 preferably having an outer diameter of about 0.007" and an inner diameter of 0.005" and length of 0.5" are partially inserted in the inflation lumen 144 formed between the inner and outer tubes. The tubes 154 are preferably placed on the same side of the inner tube 138 as will be described with reference to FIGS. 6-9, however, the tubes may be placed on opposite sides of the inner tube 138 as shown in FIGS. 4 and 5. The proximal waist 148 of the balloon 136 is placed over the tubes 154 and the inner tube 138. The outer tube 140 which has approximately the same inner diameter as the proximal waist 148 of the balloon 136 is also partially placed over the tubes 154 and the inner tube 138. A small gap 156 separates the proximal waist 148 of the balloon 136 from the outer tube 140. The gap 156 is approximately 5 mm in length. The distal waist 158 of the balloon 136 is coaxial with the distal end of the inner tube 138. The tubes 154 thus bridge the distal end of the outer tube 140 to the proximal waist 148 of the balloon 136.

The catheter 132 is assembled by applying a heat weld, as is well known by those skilled in the art, to seal the outer tube 140 around the polyimide or teflon tubes to the inner tube 138. The proximal balloon waist 148 is sealed separately to the inner tube 138 around the polyimide or teflon tubes 154 with a urethane adhesive bond such as Urethane 2139 from H. B. Fuller or Urethane 3549 from the 3 M Co. described above. Alternatively, an adhesive bond using Urethane 2139 described above may be used for bonding the inner and outer tubes.

The distal waist 158 of the balloon 136 is then bonded to the distal end of the inner tube 138 preferably by an adhesive such as Urethane 3507 from H. B. Fuller or an epoxy such as Tracon BA 2135D from Tracon of Medford, Mass.

Although two polyimide or teflon tubes 154 have been illustrated, the number of tubes used is dictated by the amount of communication desired between the inflation lumen 144 and the interior of the balloon 136.

The proximal waist 148 of the balloon 136 shown in FIG. 5 is approximately 6 mm in length while the distal end of the outer tube 140 bonded to the tubes 154 and inner tube 138 is approximately 3 mm in length.

The catheter of FIG. 3 would have approximately the same configuration as the catheter of FIG. 5 after applying a heat weld except that the interior surfaces of the proximal waist and the outer tube would be bonded to the exterior surface of the extension tube.

Figures 6, 7, 8, 9, 10:
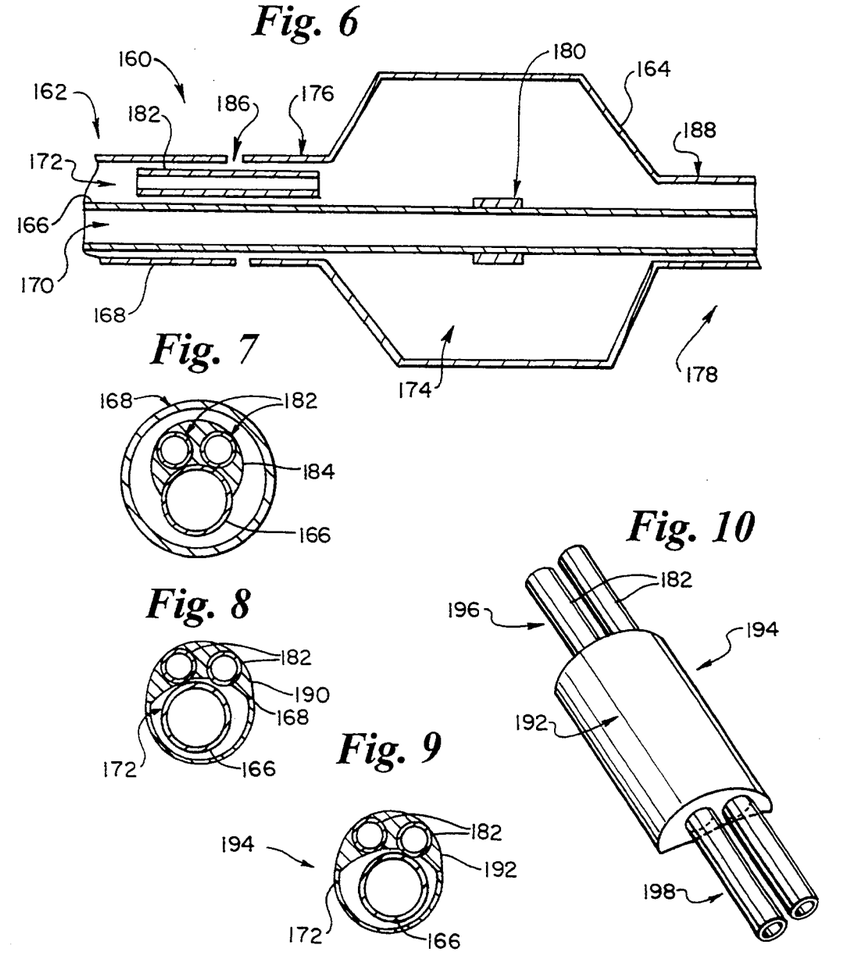
FIG. 6 is a cross-sectional view of a fifth preferred embodiment of a partially constructed coaxial catheter according to the present invention.
FIG. 7 is a cross-sectional view of a portion of the catheter shown in FIG. 6 according to a sixth preferred embodiment.
FIG. 8 is a cross-sectional view of a portion of the catheter shown in FIG. 6 according to a seventh preferred embodiment.
FIG. 9 is a cross-sectional view of a portion of the catheter shown in FIG. 6 according to an eighth preferred embodiment.
FIG. 10 is a full view of the bridge assembly used in the catheter according to FIG. 9.

FIG. 6 illustrates a partially constructed catheter 160 according to a fifth preferred embodiment of the present invention. The catheter 160 comprises a shaft 162 and an inflatable balloon 164. The shaft 162 has an inner tube 166 and an outer tube 168. The inner tube 166 forms a guide wire lumen 170 of sufficient diameter to house a standard guide wire (not shown) therein as described with reference to the guide wire lumen of FIG. 1. The outer tube 168 defines a crescent shaped lumen 172 (see FIGS. 7-9) about the inner tube 166 wherein inflation fluid from an inflation port in a manifold (not shown) is conveyed to the interior 174 of the balloon 164. The outer tube 168 may be formed of multiple sections as illustrated in FIG. 1, or alternatively, it may be formed by one single tubular member. The outer tube 168 has an inner diameter substantially equal to that of the proximal waist 176 of the balloon 164.

As with the catheter illustrated in FIGS. 4 and 5, the inner tube 166 extends through the interior 174 of the balloon 164 to the distal end 178 of the catheter 160. The inner tube 166 preferably has an outer diameter of about 0.0225" and an inner diameter of about 0.0165".

A platinum marker band 180 as described above is provided around the inner tube 166 in the interior 174 of the balloon 164 as described above.

The construction of the catheter 160 according to several embodiments will now be described with reference to FIGS. 7-9. There are several ways of constructing the catheter of FIG. 6 which will now be described with reference to FIGS. 7-9. As with the catheters illustrated in FIGS. 3-5, polyimide or teflon tubes 182 bridge the distal end of the outer tube to the proximal waist 176 of the balloon 164. FIG. 7 is a cross-sectional view of a portion of the catheter shown in FIG. 6 according to a sixth preferred embodiment. Polyimide or teflon tubes 182 preferably having an outer diameter of about 0.007" and an inner diameter of about 0.005" and a length of 0.5" are partially inserted in the crescent shaped inflation lumen 172 formed between the inner and outer tubes as illustrated in FIG. 6. Unlike the tubes shown in FIGS. 3-5, both tubes 182 are placed substantially adjacent to one another on one side of the inner tube 166.

The proximal waist 176 of the balloon 164 is partially placed over the teflon or polyimide tubes 182 and inner tube 166. The outer tube 168 which has approximately the same inner diameter as the proximal waist 176 of the balloon 164 is also partially placed over the teflon or polyimide tubes 182 and inner tube 166. A small gap 186 separates the proximal waist 176 of the balloon 164 from the outer tube 168. The gap 186 is approximately 0.2" in length. The distal waist 188 of the balloon 164 is coaxial with the distal end of the inner tube 166.

A heat weld, as is well known to those skilled in the art, is then applied to the distal end of the outer tube 168 to seal and bond the outer tube 168 around the potted polyimide or teflon tubes 182 and the inner tube 166. The proximal waist 176 of the balloon 164 is bonded separately to the inner tube 166 around the polyimide or teflon tubes 182 with a urethane adhesive bond such as H. B. Fuller 2139 or 3M's 3549 described above. Alternatively, an adhesive bond using Urethane 2139 available from the H. B. Fuller Co. may be used to bond the outer tube to the teflon or polyimide tubes 182 and inner tube 166.

The distal waist 188 of the balloon 164 is then bonded to the distal end of the inner tube 166 preferably by an adhesive such as Urethane 357 from H. B. Fuller or an epoxy such as Tracon BA 2135D from Tracon of Medford Mass. as described above.

Next a high viscosity adhesive such as Urethane 2139 from the H. B. Fuller Co. is potted around the teflon or polyimide tubes 182 between the distal end of the outer tube 168 and the proximal waist 176 of the balloon 164 illustrated by the shaded area 184. The potted adhesive acts to somewhat stiffen this region of the catheter 160.

FIG. 8 is a cross-sectional view of a portion of the catheter shown in FIG. 6 according to a seventh preferred embodiment. The same reference numerals used with reference to FIGS. 6 and 7 will be used to describe the same structure in FIGS. 8 and 9. The construction of the catheter 160 according to this seventh preferred embodiment will now be described. Polyimide or teflon tubes 182 having preferably the same dimensions as those of FIG. 7 are partially inserted in the outer tube 168 prior to assembling the inner tube 166 into the outer tube 168. The distal 5 mm of the outer tube is then crimped and melted around the teflon or polyimide tubes 182 to bond the tubes 182 to the distal end of the outer tube with approximately 3-4 mm of the teflon or polyimide tubes 182 extending out either side of the melted region. A hole is then cut in the outer tube 168 underneath the crimped and melted region so that the inner tube can be passed through the hole and under the crimped and melted region. Alternatively the outer tube 168 can be slit so that only a portion of the outer tube is crimped and melted to the tubes 182 thereby providing an opening for the inner tube 166 without later cutting a hole in the outer tube 168 after it has been bonded to the tubes 182.

A heat weld, as is well known to those skilled in the art, is then applied to the distal end of the outer tube 168 to bond the bonded outer tube 168 and the tubes 182 to the inner tube 166. The proximal waist 176 of the balloon 164 is bonded separately to the inner tube 166 around the polyimide or teflon tubes 182 with a urethane adhesive bond such as H. B. Fuller 2139 or 3M's 3549 described above. Alternatively, an adhesive bond using Urethane 2139 available from the H. B. Fuller may be used to bond the inner tube 166 with the bonded outer tube 168 and tubes 182.

The distal waist 188 of the balloon 164 is then bonded to the distal end of the inner tube 166 as described above.

FIG. 9 is a cross-sectional view of a portion of the catheter shown in FIG. 6 according to an eighth preferred embodiment. The construction of the catheter 160 according to this eighth preferred embodiment will now be described. Unlike the tubes 182 illustrated in FIGS. 7 and 8, the tubes 182 according to this preferred embodiment are first joined together as shown in FIG. 10. A material such as a low density PE illustrated by the shaded area 192 is partially molded around the tubes 182 to create a single separate bridge assembly 194. The exposed ends 196 of the tubes 182 are then inserted into the inflation lumen 172 formed between the inner and outer tubes. The distal end of the outer tube is placed over the exposed ends 196 of the tubes 182. A heat weld, as is well known to those skilled in the art, is then applied to the distal end of the outer tube 168 to bond the outer tube 168 around the exposed ends 196 of the tubes 182 to the inner tube 166. The proximal waist 176 of the balloon 164 is placed over the exposed ends 198 of the tube 182 on the opposite side of the molded area 192 from the outer tube 168. A small gap 186 separates the proximal waist 176 of the balloon 164 from the outer tube 168. The length of the gap is defined by the length of the low density PE molded area 192 portion of the bridge assembly 194. Preferably the gap 186 filled in by the molded area 192 is approximately 5 mm in length.

The distal waist 188 of the balloon 164 is coaxial with the distal end of the inner tube 166.

The proximal waist 176 of the balloon 164 is bonded separately to the inner tube 166 around the exposed ends of the tubes 182 with a urethane adhesive bond such as H. B. Fuller 2139 or 3M's 3549 described above. Alternatively, an adhesive bond using Urethane 2139 available from the H. B. Fuller Co. may be used to bond the inner tube 166, tubes 182 and outer tube 168.

The distal waist 188 of the balloon 164 is then bonded to the distal end of the inner tube 166 as described above.

While the cross-section of the catheters shown in FIGS. 8 and 9 are identical, molded area 192 of the bridge assembly 194 as shown in FIG. 9 is separate from the distal end of the outer tube. The molded area 192 is adjacent to the outer tube and proximal balloon waist, however, it does not pass underneath them. Only the exposed tubes 196 and 198 are under the outer tube and proximal balloon waist respectively.

The catheters shown in FIGS. 1-9 are not drawn to scale but rather are drawn to illustrate features of the present invention.

The proximal shafts of the catheters shown in FIGS. 2-9 may be the same as the proximal shaft described with reference to FIG. 1. In addition, the catheters of FIGS. 2-9 may have a lubricous coating applied thereto and their plastic parts may be plasma treated as described above with reference to FIG. 1. The materials described with respect to the catheter of FIG. 1 are equally applicable to the catheters of FIGS. 2-9.

While the invention has been shown and described in connection with particular preferred embodiments, it is apparent that certain changes and modifications, in addition to those mentioned above, may be made by those who are skilled in the art without departing from the basic features of the present invention. Accordingly, it is the intention of the Applicants to protect all variations and modifications within the true spirit and valid scope of the invention.

What is claimed is:

1. A coaxial dilation catheter comprising:
an outer tubular member having a proximal and distal end;
an inner tubular member concentrically disposed within said outer tubular member so as to define an inflation lumen therebetween, said inner tubular member having a proximal end and a distal end;
an extension tubular member, said extension member having a proximal end and a distal end wherein said proximal end of said extension tubular member is placed around said distal end of said inner tubular member in a transition area so that said inner tubular member defines a guide wire lumen proximal of said transition area and said extension tubular member defines a guide wire lumen distal of said transition area;
an inflatable balloon having a proximal and distal waist, said proximal waist located at least partially within said transition area, said inflatable balloon surrounding said extension tubular member and extending from said distal end of said outer tubular member, said distal end of said outer tubular member terminating in said transition area, to said distal end of said extension tubular member wherein said proximal waist of said balloon surrounds said distal end of said outer tubular member whereby an inflation lumen extending through said transition area is formed by inserting at least one mandrel into the inflation lumen, and securing said proximal waist to said outer tubular member and said outer tubular member to said distal end of said inner tubular member and said proximal end of said tubular extension member by heat bonding in said transition area.

2. A method of making a coaxial dilation catheter comprising the steps of:

providing an outer tubular member having a proximal and distal end, said distal end terminating in a transition area;

providing an inner tubular member having a proximal and distal end, said distal end also terminating in said transition area;

providing an extension member having a proximal and distal end, said proximal end terminating in said transition area;

placing said proximal end of said extension tube around said distal end of said inner tube in said transition area wherein said inner tube defines a guide wire lumen proximal of said transition area while said extension tube defines a guide wire lumen distal of said transition area;

concentrically disposing said inner tube and said extension tube within said outer tubular member so as to define an inflation lumen therebetween wherein said distal end of said outer tube substantially coincides with said transition area;

surrounding said extension member with an inflatable balloon having a proximal and distal waist wherein said balloon extends from said distal end of said outer member in said transition area to the distal tip of said catheter;

inserting at least one mandrel in said inflation lumen within said transition area;

applying a heat weld to said proximal waist of said balloon to bond said proximal waist to said outer tube proximate its distal end and to bond said outer tube within said transition area around said mandrel to said proximal end of said extension member and said distal end of said inner tube;

removing said at least one mandrel from said inflation lumen to define at least one aperture; and bonding said distal waist to the distal end of said extension tube.

* * * * *